United States Patent [19]

Sideris

[11] Patent Number: 5,433,727
[45] Date of Patent: Jul. 18, 1995

[54] CENTERING BUTTONED DEVICE FOR THE OCCLUSION OF LARGE DEFECTS FOR OCCLUDING

[76] Inventor: Eleftherios B. Sideris, Ste. 200 1600 Coulter, Amarillo, Tex. 79106

[21] Appl. No.: 291,154

[22] Filed: Aug. 16, 1994

[51] Int. Cl.6 .................................... A61B 17/00
[52] U.S. Cl. ............................ 606/213; 606/215; 606/157; 623/11; 128/887; 128/898
[58] Field of Search .......... 606/213, 215, 216, 139, 606/151, 157; 128/887, 889, 899; 623/1, 11

[56] References Cited

U.S. PATENT DOCUMENTS

| | | | |
|---|---|---|---|
| 3,874,388 | 4/1975 | King et al. | 606/213 |
| 4,621,638 | 11/1986 | Silvestrini | 606/230 |
| 4,901,721 | 2/1990 | Hakki | 606/232 |
| 4,917,089 | 4/1990 | Sideris | 606/215 |
| 5,021,059 | 6/1991 | Kensey et al. | 606/213 |
| 5,053,046 | 10/1991 | Janese | 606/215 |
| 5,108,420 | 4/1992 | Marks | 606/213 |
| 5,192,301 | 3/1993 | Kamiya | 606/213 |
| 5,284,488 | 2/1994 | Sideris | 606/213 |
| 5,334,217 | 8/1994 | Das | 606/213 |

*Primary Examiner*—Gary Jackson
*Attorney, Agent, or Firm*—Wendell Coffee

[57] ABSTRACT

This is an intravascular prosthesis deliverable transvenously for the occlusion of large heart defects. The defects are predominantly large atrial septal defects and ventricular septal defects. The device has an occluder connected with a centering counter-occluder. The device is delivered to the heart by known methods. The occluder is released on the distal side of the defect and the proximal centering counter-occluder is stretched, pulling the device over the center of the defect. Subsequently, the centering counter-occluder is buttoned against the occluder and is opposing the right atrial side of the septum. The radiopaque button is placed upon a string to verify buttoning.

7 Claims, 3 Drawing Sheets

CENTERING BUTTONED DEVICE FOR THE OCCLUSION OF LARGE DEFECTS FOR OCCLUDING

BACKGROUND OF THE INVENTION

1. Field of the Invention

The present invention relates to intravascular prosthesis delivered transvenously for the occlusion of large defects in large hearts. Such defects are mainly atrial septal defects and ventricular septal defects.

2. Description of the Related Art

U.S. Patents: KING et al, U.S. Pat. No. 3,874,388; SIDERIS, U.S. Pat. No. 4,917,089; SIDERIS, U.S. Pat. No. 5,284,488.

Publications: Rashkind—Circulation—vol 67, No. 4, April 1983.

Similar devices have been developed in the last few years for the occlusion of heart defects. They include the KING and MILLS device (U.S. Pat. No. 3,874,388); the SIDERIS button device (U.S. Pat. No. 4,917,089); the "Clamshell" device, which is a variation of the KING and MILLS device; the RASHKIND device; and the SIDERIS adjustable device for the occlusion of cardiac defects (U.S. Pat. No. 5,284,488). The previous devices attempted to occlude heart defects, including patent ductus arteriosus, atrial septal defects, and ventricular septal defects. These devices are used to treat small to moderate heart defects.

There is significant difficulty in occluding large heart defects. Reasons for this difficulty include the absence of adequate rim for the device to seat and the difficulty in positioning on the septum. Attempts at centering have been tried in different designs, while in other designs, like the classical button device (U.S. Pat. No. 4,917,089), emphasis has been given to the maneuverability of the device. In U.S. Pat. No. 5,108,420, MARKS describes an occlusion device which uses a Nitilol wire which has an elongated configuration for passage into the body through a catheter and a preprogrammed configuration which seats on each side of the defect. By pulling the disc through the defect, the inventor claims to achieve centering.

In a similar way, the "Clamshell" device, which in actuality is a modification of the KING and MILLS device (U.S. Pat. No. 3,874,388), attempts to center by pulling the distal disc through the defect, bending it, and then releasing the proximal disc. However, these attempts are only partially addressing the problem and have not been totally successful.

In 1990, a patent was issued for the "Buttoned Device For The Occlusion Of The Intra-cardiac Defects" (U.S. Pat. No. 4,917,089). In 1994, a patent was issued for "Adjustable Devices For The Occlusion of Cardiac Defects" (U.S. Pat. No. 5,284,488). Both devices are useful for the occlusion of heart defects. However, these devices require significant manipulation to position. Also, the devices are not effective in the occlusion of large heart defects. For this reason, the centering button device was designed, aiming at the occlusion of large atrial septal defects and ventricular septal defects which could not be occluded with the previous devices.

For the introduction of the centering buttoned device, the same method as the regular buttoned device and the same release mechanism are used.

SUMMARY OF THE INVENTION

(1) Progressive Contribution to the Art

The intra-cardiac device of the current invention provides a means of transvenous occlusion of large heart defects without surgery.

In the application of the centering button device, the defect is treated transvenously, and occlusion is achieved by the introduction of the whole device into the heart. The occluder has been described in inventor's U.S. Pat. No. 4,917,089.

In a preferred embodiment of the occluder portion of the device, two counter-occluder wires are partly sutured on each of the occluder wires. The counter-occluder wires are 0.018" hollow fluorocarbon resin (TEFLON) wires that cover a 3.0 NYLON thread. The sutured portion of the counter-occluder wire covers the central 40% of the length of each skeleton wire of the occluder. The total length of each counter-occluder wire is two and one-half times the occluder's length. The non-sutured ends of the counter-occluder wires are tied together and covered by a latex piece. The free wire portions of the counter-occluder are totally covered by polyurethane foam which is attached by a continuous suture. In the preferred embodiment of the covered latex portion of the counter-occluder, a square piece of latex of approximately 5 mm is covered on both sides by polyurethane foam and is sutured on the free wire portions of the centering counter-occluder.

Another aspect of this invention is the button loop, which is similar to the adjustable loop described in inventor's U.S. Pat. No. 5,284,488. One difference exists though: a radiopaque button is connected to the final small loop of the button loop which is connected to the release wire. This radiopaque button is a spring button, and is parallel to the button loop during buttoning. The button becomes horizontal when released. This prevents the occluder from unbuttoning from the counter-occluder.

Another aspect of the device is the loading wire connected to the button loop and crossing the covered latex portion of the centering counter-occluder. This wire has been extensively described in inventor's U.S. Pat. No. 4,917,089.

Another aspect of the device is the centering wire. This is a 0.035" hollow Teflon coated wire with a double NYLON thread through it, exactly like the release wire. The centering wire is connected to the covered latex portion of the centering counter-occluder.

Another aspect of the current invention is a 6-French (F) catheter with a 0.038" lumen positioned over the loading wire and through the latex portion of the counter-occluder. This catheter is able to cover the button loop. It is also used to apply pressure to the center of the occluder. The 6F catheter provides a guide path for the centering counter-occluder when the counter-occluder is stretched, by means of pulling the centering guidewire; or compressed, by means of pushing the latex piece with a tip of a 11F long sheath.

The device is introduced into the 11F long sheath. The sheath is positioned across the defect. The occluder and subsequently the full device are released in the left atrium on the proximal side of the defect. The loading wire is pulled, with the 6F catheter pushed over the button loop, until the loading wire is perpendicular to the occluder. The sheath is pulled back through the defect while the centering wire is pulling the centering counter-occluder, sliding the latex piece of the counter-occluder along the 6F catheter. The whole device and sheath complex is then pulled by the loading wire until the occluder is positioned over the center of the atrial septum on the proximal side of the defect. Subsequently, the long sheath pushes the centering counter-occluder along the 6F catheter until the counter-occluder takes the shape of a double figure "8" on the distal side of the defect. Subsequently, the 6F catheter is pulled back to release the radiopaque button, and buttoning is achieved. Manipulations are made under fluoroscopy and echocardiography. The release, or detachment, of the device is achieved through the same mechanism as the button device (U.S. Pat. No. 5,284,488), with release of the centering wire first, and the loading wire subsequently.

In accordance with the principals of the present invention, the centering button device has significant advantages over known devices, specifically the RASHKIND device, KING and MILLS device, buttoned device, adjustable devices, and the approacher occlusion device. One can achieve perfect centering in large defects, and therefore compliment the application of all the other devices.

(2) Objects of this Invention

An object of this invention is to provide centering occluding devices for treating large defects.

Another object is to provide centering occluding devices of reasonable sizes for introduction into large children or adults.

Another object of this invention is to be able to center the device despite a very large defect and perhaps an incomplete rim.

Further objects are to achieve the above with devices that are sturdy, compact, durable, lightweight, simple, safe, efficient, versatile, ecologically compatible, energy conserving, and reliable, yet inexpensive and easy to manufacture, install, operate, and maintain.

Other objects are to achieve the above with a method that is rapid, versatile, ecologically compatible, energy conserving, efficient, and inexpensive, and does not require highly skilled people to install, operate, and maintain.

The specific nature of the invention, as well as other objects, uses, and advantages thereof, will clearly appear from the following description and from the accompanying drawings, the different views of which are not necessarily scale drawings.

As an aid correlating the terms of the claims to the exemplary drawings the following catalogue of elements and steps is provided:

| 10 | centering button device |
| 11 | occluder |
| 12 | button loop |
| 14 | centering counter-occluder |
| 16 | polyurethane disc |
| 18 | skeleton wire of the occluder |
| 20 | terminal small loop |
| 22 | radiopaque spring button |
| 24 | middle loop |
| 26 | first loop |
| 28 | polyurethane covered latex piece |
| 30 | loading wire or release wire |
| 32 | pusher catheter |
| 34 | centering wire |
| 36 | small loop |
| 38 | long sheath |

DESCRIPTION OF THE PREFERRED EMBODIMENTS

Figure 1:
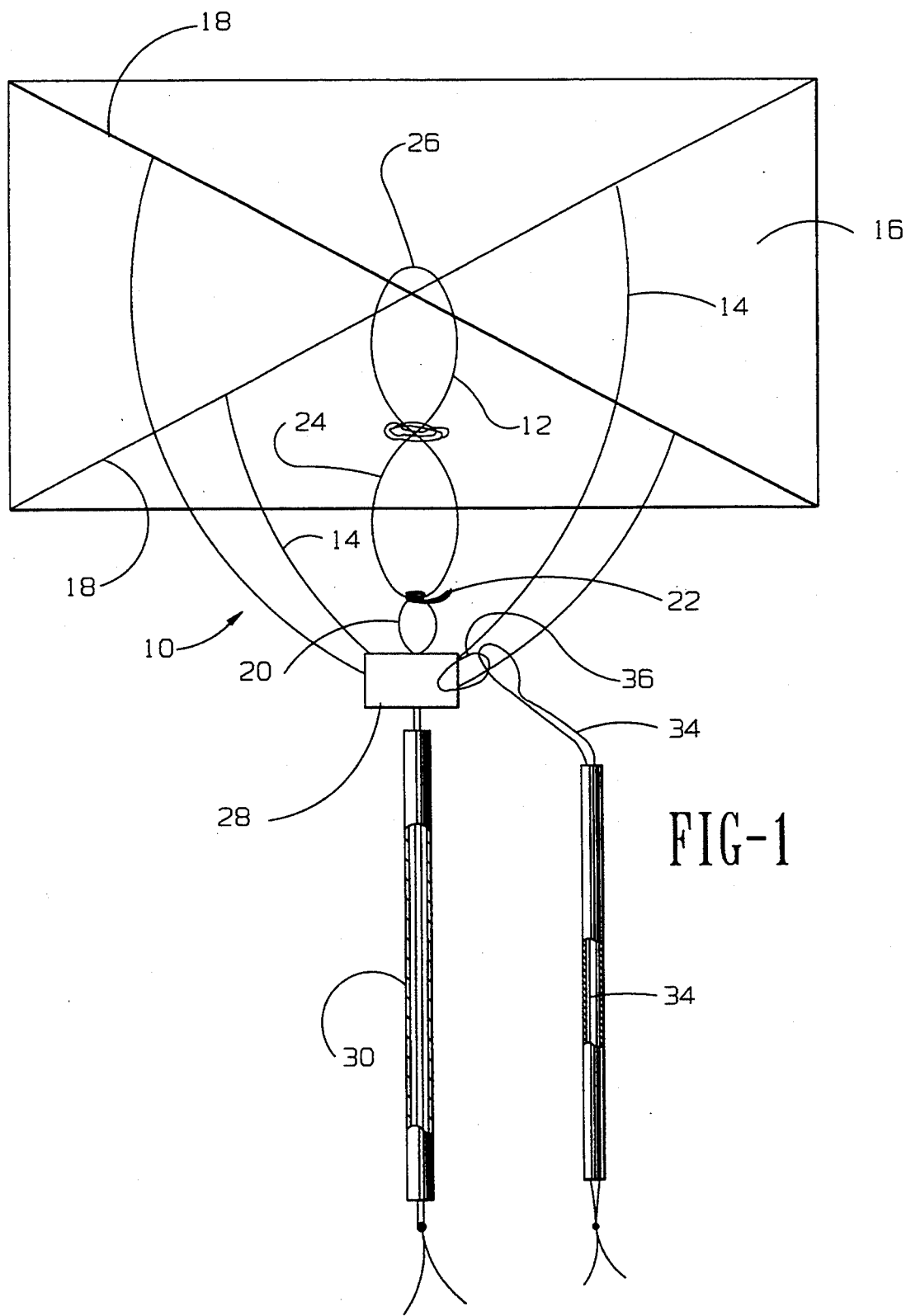
FIG. 1 is a perspective view of the preferred embodiments of the intra-cardiac centering buttoned device prosthesis with the occluder connected with the centering counter-occluder through the button loop with the loading wire. The centering wire is connected to the covered latex portion of the occluder.

Referring to the drawings, and FIG. 1 in particular, there is illustrated occluder 11 of the centering button device 10 connected to button loop 12 and centering counter-occluder 14.

The occluder 11 is made of polyurethane foam lining 16 that is 2 mm thick and has a diameter of 10 mm more than the diameter of the defect to be occluded. Fluorocarbon resin (TEFLON) coated wire skeleton 18 is introduced into the foam in an X shape and securely stitched to the foam by continuous and interrupted sutures.

The button loop 12 is made of 3.0 NYLON thread and the button loop consists of:
a) terminal small loop 20 with a diameter of 1–2 mm;
b) radiopaque button 22 TEFLON coated wire connected to one of the threads of the terminal loop 20;
c) middle loop 24 with a diameter of 2–3 mm separated from both the terminal small loop 20 and first loop 26 by three knots; and
d) the first loop 26 with a diameter of 3 mm that is sutured to the occluder 11.

The button loop 12 is connected to the occluder 11 as is described in U.S. Pat. No. 5,284,488.

Centering counter-occluder 14 is made of 2 hollow 0.018" TEFLON covered wires. A central portion of each counter-occluder wire is sutured to the central 40% of a occluder skeletal wire 18. The centering counter-occluder wire has a 3.0 NYLON thread threaded through it that is sutured and tied opposite the occluder end. The four exiting wires of the centering counter-occluder 14 form a pyramid shaped cage.

On the end of the counter-occluder 14 opposite of the occluder 11, is foam covered latex piece 28. This piece consists of a 1 cm square latex piece sutured with the four centering wires of the centering counter-occluder 14. Both sides of the latex piece are covered by polyurethane foam.

The button loop 12 is connected to loading wire 30. The loading wire consists of a hollow 0.018" TEFLON wire threaded with a NYLON loop that passes through the terminal small loop 20. The thread is twisted several times at the distal end of the loading wire so that it is stretched inside the hollow wire, and tied off 6F pusher catheter 32 is loaded over the loading wire 30 and pierces the latex piece 28 of the counter-occluder 14 and goes through the cage of the counter-occluder.

By pulling the loading wire 30 and pushing the pusher catheter 32, the button loop 12 is introduced into the pusher catheter. The pusher catheter is pushed until the tip of the pusher catheter touches the center of the occluder 11, making the occluder perpendicular to the pusher catheter.

Centering wire 34 is a 0.018" TEFLON coated hollow wire with a double NYLON thread through it, made exactly like the loading wire 30. The centering wire is connected to the covered latex piece 28 of the centering counter-occluder 14 through small loop 36. The centering wire guides the latex piece over the pusher catheter 32 and helps to form a pyramid shaped cage of the counter-occluder 14. The cage helps center the occluder.

Figure 2:
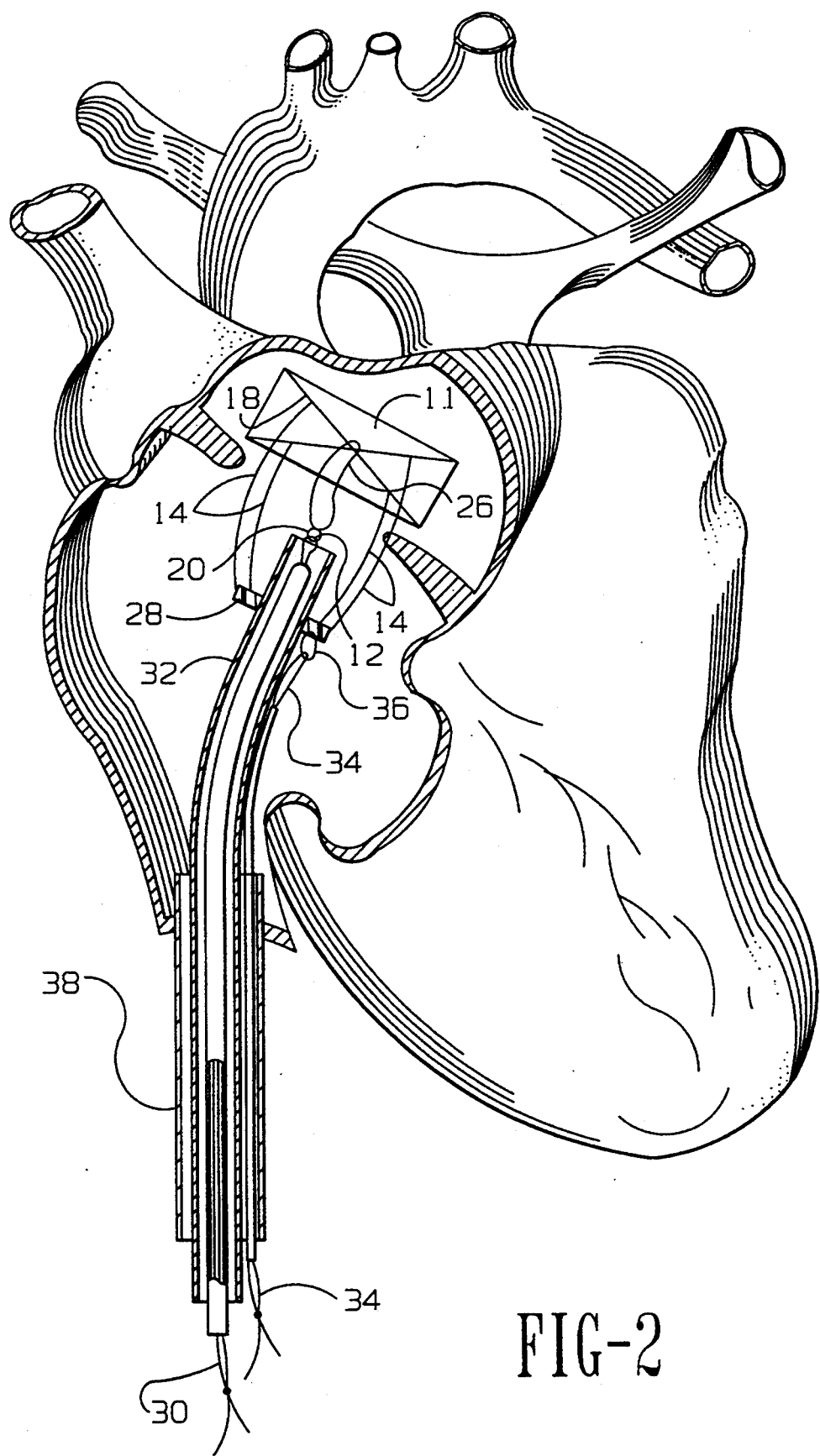
FIG. 2 is a perspective view of the device centering through a large atrial septal defect.

FIG. 2 shows the centering of the device through a large atrial septal defect. The device is introduced through 11F long sheath 38 into the left atrium. By pulling the loading wire 30 and pushing the pusher catheter 32 the occluder 11 becomes perpendicular to the pusher catheter. The centering counter-occluder 14 is pulled over the pusher catheter 32 by the centering wire 34. At the same time, the long sheath 38 is withdrawn down to the inferior vena cava. Subsequently, the whole device is pulled through the atrial septal defect until the occluder 11 is touching the left atrial side of the atrial septum. The four wires of the centering counter-occluder 14 cage, guided by the perimeter of the defect, position the device exactly over the center of the atrial septal defect.

Figure 3:
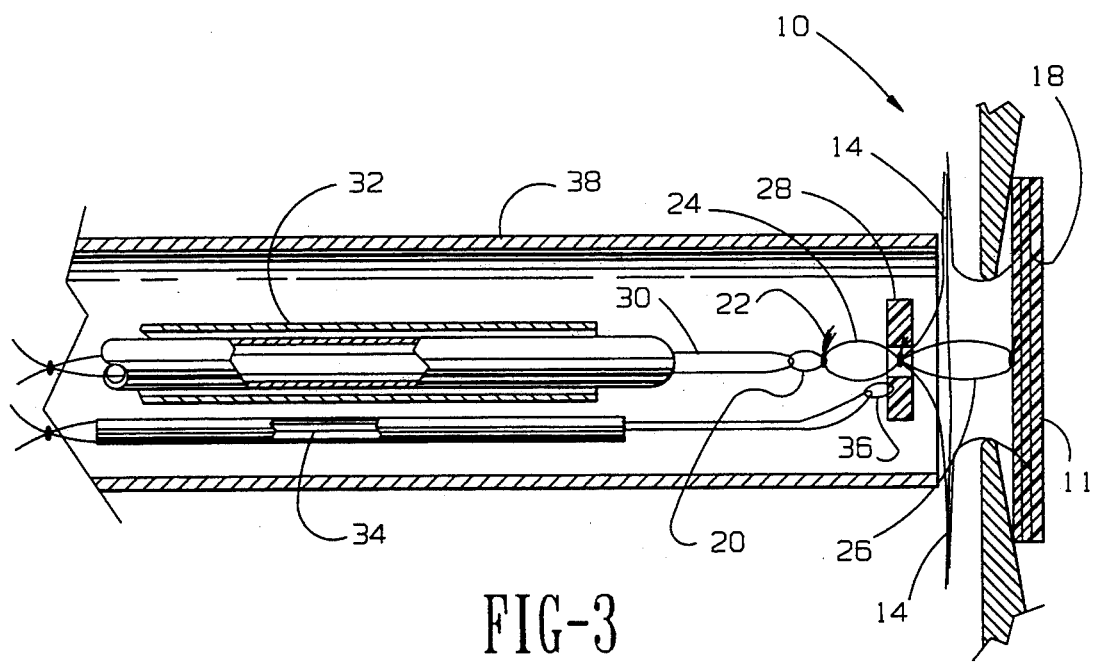
FIG. 3 is a transverse view of the device buttoned but not released.

FIG. 3 is a transverse view of a buttoned but not yet released device. The occluder 11 has been centered over the atrial septal defect by the centering counter-occluder 14 which has been pushed by the tip of the long sheath 38 over the pusher catheter 32 until the covered latex piece 28 of the centering counter-occluder 14 is touching the center of the skeletal wires 18 of the occluder 11. At a later stage, the pusher catheter is withdrawn until the button loop 12 and radiopaque spring wire 22 are freed, thereby holding the centering counter-occluder 14 in a double figure "8" on the right atrial aspect of the atrial septum.

Figure 4:
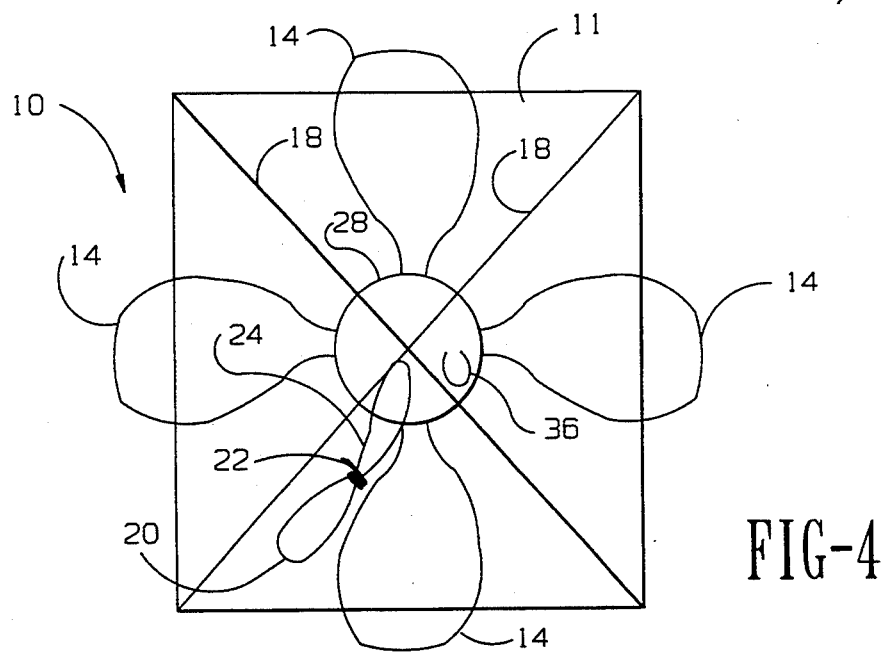
FIG. 4 is a perspective view of the right atrial aspect of the device buttoned and released on an atrial septal defect.

FIG. 4 shows the right atrial aspect of a released device. The occluder 11 is positioned on the left atrium, occluding the heart defect. The centering counter-occluder 14 in a double figure "8" is positioned on the right atrial aspect of the atrial septum. The button loop 12 with the radiopaque spring 22 holding the counter-occluder against the occluder 11 prevents the button loop from unbuttoning.

Release is achieved by releasing the centering wire 34 first and the loading wire 30 second. The distal end of the centering wire is cut at a position outside of the body. This separates the thread from the covering wire. Then, the TEFLON cover wire is removed. Next the thread is pulled out as a single strand. The same procedure is used to remove the loading wire.

The embodiment shown and described above is only exemplary. I do not claim to have invented all the parts, elements, or steps described. Various modifications can be made in the construction, material, arrangement, and operation and still be within the scope of my invention.

The restrictive description and drawings of the specific examples above do not point out what an infringement of this patent would be but are to enable one skilled in the art to make and use the invention. The limits of the invention and the bounds of the patent protection are measured by and defined by the following claims.

The embodiment shown and described above is only exemplary. I do not claim to have invented all the parts, elements or steps described. Various modifications can be made in the construction, material, arrangement, and operation, and still be within the scope of my invention.

The restrictive description and drawings of the specific examples above do not point out what an infringement of this patent would be, but are to enable one skilled in the art to make and use the invention. The limits of the invention and the bounds of the patent protection are measured by and defined in the following claims.

I claim as my invention:

Subject matter claimed for protection is:

1. A method of occluding a heart defect having a perimeter by a buttoned device comprising the steps of:
   a) introducing the device into a long sheath,
   b) positioning the device in the long sheath in a heart chamber where there is a defect,
   c) releasing the device from the long sheath on a proximal side of the defect by
   d) pushing a pusher catheter against an occluder,
   e) pulling a counter-occluder along the pusher catheter with a centering wire to form a pyramid shaped cage of the counter-occluder's wires,
   f) pulling a loading wire to guide the counter-occluder to the distal side of the defect while
   g) forcing the counter-occluder cage to follow the defect's perimeter, thereby
   h) centering the occluder across the defect,
   i) pushing a polyurethane covered latex piece of the counter-occluder with a tip of the long sheath along the pusher catheter until the latex piece touches the occluder and a double figure 8 is formed of the counter-occluder,
   j) pulling the pusher catheter back until a radiopaque button is released from the pusher catheter, while
   k) holding the tip of the long sheath against the latex piece of the counter-occluder,
   l) detaching the device by extracting the centering wire, and the loading wire while
   m) holding the device in place with the tip of the long sheath, and
   n) removing the long sheath.

2. The method as defined in claim 1 further comprising:
   o) covering a button loop with the pusher catheter so that said button, which is a radiopaque spring button on the button loop, is almost parallel to the axial direction of the pusher catheter,
   p) positioning the button device in its desired position, and
   q) withdrawing the catheter so that the button is released from the pusher catheter
   r) causing the button to become perpendicular to the button loop, thus
   s) buttoning the button device and
   t) preventing the device from unbuttoning.

3. A method of buttoning a button device comprising the steps of:
   a) covering a button loop with a catheter so that a radiopaque spring button on the button loop is almost parallel to the axial direction of the catheter,
   b) positioning the button device in its desired position, and
   c) withdrawing the catheter so that the button is released from the catheter
   d) causing the button to become perpendicular to the button loop, thus
   e) buttoning the button device and f) preventing the device from unbuttoning.

4. An intra-cardiac percutaneously deliverable device for the repair of heart defects having:
   a) an occluder including:
      i) a foldable foam resin disc,
      ii) a coated wire skeleton in the form of an "X" sutured to the foam disc, and
      iii) an adjustable loop sutured to the center of the wire skeleton;
   b) said adjustable loop is formed by
      i) a first loop, connected to said wire skeleton,
      ii) a middle loop, connected to said first loop,
      iii) a terminal small loop connected to said middle loop, and
      iv) a radiopaque button connected between said terminal small loop and middle loop;
   c) a loading wire having a proximal end and a distal end, wherein said loading wire is a fluorocarbon resin coated hollow wire,
   d) a loading, long double thread going through the terminal small loop, through the loading wire, and tied at the distal end of the loading wire;
   wherein the improvement comprises:
   e) a centering counter-occluder sutured in part to the skeleton wires of the foam disc and covering a central 40% of said skeleton wires;
   f) said centering counter-occluder including:
      i) two hollow wires threaded with NYLON thread and sutured to the skeleton wires, said thread also sutured and tied at each end of the two hollow wires to
      ii) a polyurethane covered latex piece;
   g) a centering guidewire having a proximal end and a distal end, wherein said guidewire is a fluorocarbon resin hollow wire;
   h) a centering, long double thread going through a small loop that is tied to the covered latex piece of the centering counter-occluder, through the hollow centering wire, and tied at the distal end of the centering wire; wherein
   j) the centering counter-occluder may be pulled along an axial pusher catheter by the centering guidewire, or
   k) pushed over the pusher catheter, which contains the loading wire and the button loop, stopping at the occluder by a long sheath.

5. The intra-cardiac percutaneously deliverable device for the repair of heart defects as defined in claim 4 further comprising:
   l) said radiopaque button is approximately parallel to the button loop when the spring button is inside a pusher catheter, and
   m) said radiopaque button is approximately perpendicular to the button loop when the radiopaque button is released from the pusher catheter.

6. The intra-cardiac percutaneously deliverable device for the repair of heart defects as defined in claim 4 wherein each counter-occluder wire has a length that is $2\frac{1}{2}$ times a length of the occluder.

7. An intra-cardiac percutaneously deliverable device for the repair of heart defects having:
   a) an occluder including:
      i) a foldable foam resin disc,
      ii) a coated wire skeleton in the form of an "X" sutured to the foam disc, and
      iii) an adjustable loop sutured to the center of the wire skeleton;
   b) said adjustable loop is formed by
      i) a first loop, connected to said wire skeleton,
      ii) a middle loop, connected to said first loop,
      iii) a terminal small loop connected to said middle loop, and
      iv) a radiopaque button connected between said terminal small loop and middle loop;
   c) a loading wire having a proximal end and a distal end, wherein said loading wire is a fluorocarbon resin coated hollow wire,
   d) a loading, long double thread going through the terminal small loop, through the loading wire, and tied at the distal end of the loading wire;
   wherein the improvement comprises:
   e) said radiopaque button is approximately parallel to the button loop when the spring button is inside a pusher catheter, and
   f) said radiopaque button is approximately perpendicular to the button loop when the radiopaque button is released from the pusher catheter.

* * * * *